United States Patent [19]

Grove

[11] 4,263,041
[45] Apr. 21, 1981

[54] OPTIONALLY SUBSTITUTED PHENYL, AND ALKYL N-[5-(2-CHLORO-4-TRIFLUOROMETHYL-6-OPTIONALLY SUBSTITUTED PHENOXY)-2-NITRO, HALO, OR CYANOBENZOYL]CARBAMATES

[75] Inventor: William S. Grove, Doylestown, Ohio
[73] Assignee: PPG Industries, Inc., Pittsburgh, Pa.
[21] Appl. No.: 124,198
[22] Filed: Feb. 25, 1980
[51] Int. Cl.³ .................. A01N 37/46; C07C 79/46
[52] U.S. Cl. .................. 71/108; 71/105; 71/98; 260/465 D; 260/453 AR; 560/18; 560/21; 560/27
[58] Field of Search .......... 560/18, 21, 27; 71/105, 71/108, 98; 260/465 D

[56] References Cited

U.S. PATENT DOCUMENTS

| | | | |
|---|---|---|---|
| 3,748,356 | 7/1973 | Wellinga et al. | 260/553 E |
| 3,784,635 | 1/1974 | Theissen | 560/21 |
| 3,798,276 | 3/1974 | Bayer et al. | 260/612 R |
| 3,928,416 | 12/1975 | Bayer et al. | 560/21 |
| 3,972,934 | 8/1976 | Marshall | 560/27 |
| 3,976,470 | 8/1976 | Baker | 71/100 |
| 4,002,662 | 1/1977 | Theissen | 71/105 |
| 4,046,798 | 9/1977 | Bayer et al. | 260/465 D |
| 4,047,932 | 9/1977 | Albrecht et al. | 71/111 |
| 4,059,435 | 11/1977 | Johnson | 71/105 |
| 4,070,178 | 1/1978 | Johnson et al. | 71/105 |
| 4,106,925 | 8/1978 | Rohr et al. | 71/105 |
| 4,134,753 | 1/1979 | Hörlein et al. | 260/465 D |
| 4,164,408 | 8/1979 | Theissen | 71/105 |
| 4,173,464 | 11/1979 | Noguchi et al. | 71/105 |

Primary Examiner—Natalie Trousof
Assistant Examiner—G. T. Breitenstein
Attorney, Agent, or Firm—Edward J. Whitfield; Robert J. Grassi

[57] ABSTRACT

Disclosed are compounds, for example, methyl N-[5-(2-chloro-4-trifluoromethylphenoxy)-2-nitrobenzoyl]carbamate; the process of making the compounds; and the method of controlling weeds such as yellow foxtail and johnsongrass when growing among crops with the compounds represented by Formula I:

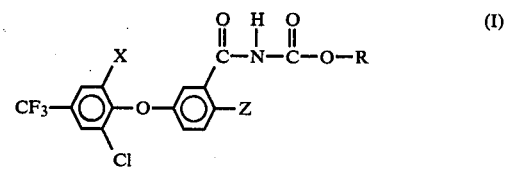

wherein X is hydrogen (H), chloro (Cl), or bromo (Br); Z is nitro ($NO_2$), halogen, or cyano (CN); and R is an alkyl of up to four carbon atoms or

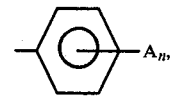

where A is halogen, an alkyl of up to three carbon atoms, an alkoxy of up to three carbon atoms, an alkylthio of up to three carbon atoms; cyano (CN), trifluoromethyl ($CF_3$), nitro ($NO_2$), or $CO_2R^2$, where $R^2$ is an alkyl of up to four carbon atoms, and n is an integer of 0, 1, 2, or 3.

15 Claims, No Drawings

OPTIONALLY SUBSTITUTED PHENYL, AND ALKYL N-[5-(2-CHLORO-4-TRIFLUOROMETHYL-6-OPTIONALLY SUBSTITUTED PHENOXY)-2-NITRO, HALO, OR CYANOBENZOYL]CARBAMATES

BACKGROUND OF THE INVENTION

Field of the Invention

The invention pertains to alkyls of up to four carbon atoms, phenyl, or phenyl substituted with one to three alkyls of up to three carbon atoms, halogens, alkoxys of up to three carbon atoms, alkylthios of up to three carbon atoms, cyanos, trifluoromethyls, nitros, -$CO_2R^2$ having $R^2$ as an alkyl of up to four carbon atoms N-[5-(2-chloro-4-trifluoromethyl-6-unsubstituted or chloro or bromophenoxy)-2-nitro, halo, or cyanobenzoyl]-carbamates, such as methyl N-[5-(2-chloro-4-trifluoromethylphenoxy)-2-nitrobenzoyl]carbamate. The invention also pertains to the method of making the compounds and the method of controlling noxious weeds such as teaweed and yellow foxtail with the compounds.

SUMMARY OF THE INVENTION

Disclosed are novel herbicidal compounds graphically represented by Formula I:

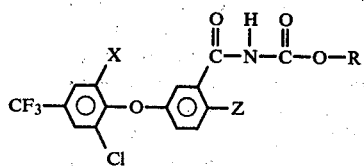

wherein X is hydrogen (H), chloro (Cl), or bromo (Br); Z is nitro ($NO_2$), halogen, or cyano (CN); and R is an alkyl of up to four carbon atoms or

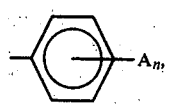

where A is halogen, an alkyl of up to three carbon atoms, an alkoxy of up to three carbon atoms, an alkylthio of up to three carbon atoms, cyano (CN), trifluoromethyl ($CF_3$), nitro ($NO_2$), or $CO_2R^2$, where $R^2$ is an alkyl of up to four carbon atoms, and n is an integer of 0, 1, 2, or 3, for example, methyl N-[5-(2-chloro-4-trifluoromethylphenoxy)-2-nitrobenzoyl]carbamate. The method of making the compounds and the method of controlling noxious weeds such as teaweed and yellow foxtail are also disclosed.

DETAILED DESCRIPTION OF THE INVENTION

The Compounds

The novel useful compounds of this invention are graphically represented by Formula I:

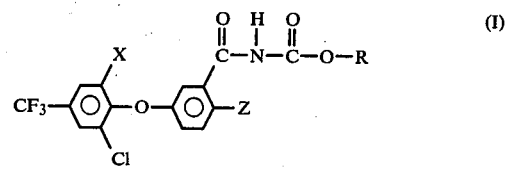

wherein X is hydrogen (H), chloro (Cl), or bromo (Br); Z is nitro ($NO_2$), halogen, or cyano (CN); and R is an alkyl of up to four carbon atoms or

where A is halogen, an alkyl of up to three carbon atoms, an alkoxy of up to three carbon atoms, an alkylthio of up to three carbon atoms, cyano (CN), trifluoromethyl ($CF_3$), nitro ($NO_2$), or $CO_2R^2$, where $R^2$ is an alkyl of up to four carbon atoms, and n is an integer of 0, 1, 2, or 3.

Examples of the compounds graphically represented by Formula I are:

methyl N-[5-(2-chloro-4-trifluoromethylphenoxy)-2-nitrobenzoyl]carbamate;

ethyl N-[5-(2-chloro-4-trifluoromethylphenoxy)-2-nitrobenzoyl]carbamate;

isopropyl N-[5-(2-chloro-4-trifluoromethylphenoxy)-2-nitrobenzoyl]carbamate;

methyl N-[5-(2,6-dichloro-4-trifluoromethylphenoxy)-2-nitrobenzoyl]carbamate;

propyl N-[5-(2-bromo-6-chloro-4-trifluoromethylphenoxy)-2-nitrobenzoyl]carbamate;

phenyl N-[5-(2-chloro-4-trifluoromethylphenoxy)-2-nitrobenzoyl]carbamate;

2-chlorophenyl N-[5-(2-chloro-4-trifluoromethylphenoxy)-2-cyanobenzoyl]carbamate;

3-methylphenyl N-[5-(2-chloro-4-trifluoromethylphenoxy)-2-chlorobenzoyl]carbamate;

4-ethylphenyl N-[5-(2-chloro-4-trifluoromethylphenoxy)-2-bromobenzoyl]carbamate;

4-methoxyphenyl N-[5-(2,6-dichloro-4-trifluoromethylphenoxy)-2-nitrobenzoyl]carbamate;

3-thiomethylphenyl N-[5-(2-bromo-6-chloro-4-trifluoromethylphenoxy)-2-cyanobenzoyl]carbamate;

2-cyanophenyl N-[5-(2-chloro-4-trifluoromethylphenoxy)-2-chlorobenzoyl]carbamate;

3-trifluoromethylphenyl N-[5-(2-chloro-4-trifluoromethylphenoxy)-2-bromobenzoyl]carbamate;

4-nitrophenyl N-[5-(2-chloro-4-trifluoromethylphenoxy)-2-nitrobenzoyl]carbamate;

3-methoxycarbonylphenyl N-[5-(2-chloro-4-trifluoromethylphenoxy)-2-nitrobenzoyl]carbamate;

2,4-dichlorophenyl N-[5-(2,6-dichloro-4-trifluoromethylphenoxy)-2-cyanobenzoyl]carbamate;

2-chloro-5-methylphenyl N-[5-(2-bromo-6-chloro-4-trifluoromethylphenoxy)-2-chlorobenzoyl]carbamate;

2,4-dichloro-6-methylphenyl N-[5-(2-chloro-4-trifluoromethylphenoxy)-2-bromobenzoyl]carbamate;

2,4,6-trichlorophenyl N-[5-(2-chloro-4-trifluoromethylphenoxy)-2-nitrobenzoyl]carbamate.

Although all of the compounds are useful for purposes described herein, some are more preferred than others. The order of increasing preference for compounds where R is as defined herein is

<an alkyl of up to four carbon atoms<ethyl<methyl. When $A_n$ is as defined herein, it is preferred that n be zero (0) or one (1). The order of increasing preference for compounds where A is as defined herein is

<nitro ($NO_2$)<trifluoromethyl ($-CF_3$)<cyano (CN)<an alkylthio of up to three carbon atoms<an alkoxy of up to three carbon atoms<an alkyl of up to four carbon atoms<halogen. When Z is as defined herein, the order of increasing preference is cyano (CN)<halogen<chloro (Cl)<nitro ($NO_2$). When X is as defined herein, the increasing order of preference is bromo (Br)<chloro (Cl)<hydrogen (H).

The most preferred compound is methyl N-[5-(2-chloro-4-trifluoromethylphenoxy)-2-nitrobenzoyl]carbamate.

Synthesis of the Compounds

The compounds represented by Formula I are prepared by reacting in the presence of a base catalyst, for example, pyridine or triethylamine, in a solvent in which the compounds are soluble; such as: benzene, methylene chloride, chloroform, tetrahydrofuran, ethyl acetate, or without a solvent by merely reacting in the presence of a base catalyst (such as pyridine or triethylamine) a substituted phenoxy-2-substituted benzoyl isocyanate graphically represented by Formula II:

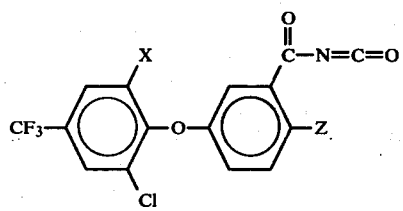

(II)

wherein X and Z are as defined herein, and an alcohol or phenol represented by Formula III:

HO—R          (III)

wherein R is as defined herein, until a compound of Formula I forms, and separating the compound of Formula I from the reaction mixture.

The general method of carrying out the reaction is as follows: To a mixture of a substituted phenoxy-2-substituted benzoyl isocyanate, represented by Formula II, and a base catalyst such as pyridine, at a temperature of from 10° to 35° C., is added an excess of an alcohol, represented by Formula III (an inert solvent can be used). The resulting mixture is refluxed until the reaction is complete. The reaction mixture is then cooled. In some cases, it may be washed separately with an equal volume of one normal acid, water, one normal sodium hydroxide or other basic material, and water respectively; and the organic phase is then dried over magnesium sulfate or other anhydrous drying salt. In other cases, after cooling, the reaction mixture is concentrated, for example, upon a rotary evaporator or is allowed to crystallize, or is vacuum dried so as to separate out the compound of Formula I. Although the resulting product may be used as such, the resulting product can also be recrystallized or purified as desired.

The substituted phenoxy-2-substituted benzoyl isocyanate of Formula II may be obtained from commercial sources or may be made by any of the techniques known to those skilled in the art, such as described in Organic Synthesis. The alcohol represented by Formula III is made by any of the known techniques described in the art and/or is obtained from commercial sources.

The following example illustrates the general synthesis of the compound described herein.

EXAMPLE I

Methyl [5-(2-chloro-4-trifluoromethylphenoxy)-2-nitrobenzoyl]carbamate

A 100 milliliter, 3-necked flask, equipped with an addition funnel, a reflux condenser, and a magnetic stirring bar, was charged with 3.86 grams (0.01 mole) of 5-(2-chloro-4-trifluoromethylphenoxy)-2-nitrobenzoyl isocyanate and four (4) drops of pyridine; and while stirring, 50 cubic centimeters of methyl alcohol was added at room temperature. After the addition was complete, the mixture was refluxed for 22 hours, cooled, and then concentrated on a rotary evaporator to a brown hardened residue. The residue was removed and recrystallized from a mixture of ethyl acetate-ligroin (50 V/50 V) to yield 2.98 grams of a white crystalline material containing methyl N-[5-(2chloro-4-trifluoromethylphenoxy)-2-nitrobenzoyl]carbamate.

NMR (acetone, $d_6$/DMSO) 9.0δ (broad singlet, 1H); 7.1–8.4δ (multiplet, 6H); 3.67δ (singlet, 3H).

APPLICATIONS OF THE COMPOUNDS AGAINST WEEDS

The new compounds of this invention are particularly valuable for weed control because they are toxic to many species and groups of weeds and are relatively nontoxic to many beneficial plants. The exact amount of one or more of the compounds required depends upon a variety of factors including the hardiness of the particular weed species, the weather, the type of soil, the method of application, the kind of beneficial plants in the same area, and the like. Thus, while the application of up to only about one or two ounces of active compound per acre may be sufficient for good control of a light infestation of weeds growing under adverse conditions, the application of 0.2 pounds or 8 pounds or 20 pounds or more of an active compound described herein per acre may be required for good control of a dense infestation of hardy perennial weeds growing under favorable conditions.

a. Examples of Weeds Which May Be Controlled by the Compounds Described Herein

Weeds are undesirable plants growing where they are not wanted, having no economic value, and interfering with the production of cultivated crops, with the growing of ornamental plants, or with the welfare of livestock. Weeds may be classified as broadleaf or grassy weeds, a classification which includes many types of known weeds which may be controlled by the composition set forth herein, when applied in a herbicidally effective amount. These include field pennycress, ryegrass, goosegrass, chickweed, purslane, smartweed, knotweed, wild buckwheat, kochia, medic, corn cockle, ragweed, sow-thistle, croton, cuphia, dodder, fumitory, groundsel, hempnettle, knawel, spurge, spurry, emex, jungle rice, pondweed, dogfennel, carpetweed, bedstraw, ducksalad, naiad, cheatgrass, fall panicum, witchgrass, switchgrass, watergrass, teaweed, wild turnip and sprangletop; biennials such as wild carrot, matricaria, wild barley, campion, chamomile, burdock, mullein, roundleaved mallow, bull thistle, houndstongue, moth mullein, and purple star thistle; or perennials such as white cockle, perennial ryegrass, quackgrass, Canada thistle, hedge bindweed, Bermuda grass, sheep sorrel, curley dock, nutgrass, field chickweed, dandelion, campanula, field bindweed, Russian knapweed, mesquite, toadflax yarrow, aster, gromwell, horsetail, ironweed, sesbania, bulrush, cat-tail, wintercress, horsenettle, nutsedge, milkweed, and sicklepod.

The compounds of the invention, particularly the preferred compounds, such as methyl N-[5-(2-chloro-4-trifluoromethylphenoxy)-2-nitrobenzoyl]carbamate, are most effective at rates as low as up to two pounds per acre preemergence against weeds of the genera: Sida, Setaria, Sorghum, Sesbania, Abutilon, Echinochloa and Digitaria.

The compounds of the invention, i.e. methyl N-[5-(2-chloro-4-trifluoromethylphenoxy)-2-nitrobenzoyl]carbamate, are most effective preemergence at low rates of application, up to two pounds per acre against the weed species: *Sida spinosa* (L) (teaweed), *Setaria glauca* (L) (yellow foxtail), *Digitaria sanguinalis* (L) (crabgrass), *Sorghum halepense* (L) (johnsongrass), *Sesbania* spp. (coffeeweed), *Abutilon theophrasti* (L) (velvetleaf), and *Echinochloa crusgalli* (L) (barnyardgrass). At higher rates (five pounds per acre or more), weeds such as *Datura stramonium* (L) (jimsonweed), *Ipomoea purpurea* (L) *Roth* (morningglory), *Avena fatua* (L) (wild oats), *Brassica kaber* (D.C.) (wild mustard), and *Cyperus esculentus* (L) (yellow nutsedge) are controlled.

The compounds of the invention, particularly the preferred compounds described herein and especially the most preferred compound, are also useful for controlling weeds which are growing among crops such as tomatoes, cotton, and soybeans.

b. Description of the Method of Controlling Weeds

As used herein and in the claims, the method of controlling the weeds comprises contacting the weeds with a herbicidally effective amount of a composition represented by the general formula described herein. The term "contacting the weeds" refers to any method of contacting the weeds, both preemergence (before the weeds appear) and/or postemergence (after the weeds appear), but preferably the weeds are contacted preemergence such as applying granules of the compound to the soil prior to emergence, or spraying a solution of the compound or compounds described by the general formula, or any other method known in the art by which the weeds are contacted either before they emerge or after they emerge, or both before and after they emerge, with one or more of the compounds represented by general Formula I described herein. The phrase "the herbicidally effective amount" refers to that amount required under the environmental conditions in order to effectively control, that is, the weeds are so severely injured as not to recover or compete against the crops or are killed.

c. General Application of the Compounds

For practical use of herbicides, the compounds of this invention are generally incorporated into herbicidal formulations which comprise an inert carrier and a herbicidally toxic amount of a compound mentioned herein. Such herbicidal formulations enable the active compound to be applied conveniently to the site of the weed infestation in any desired quantity. These formulations can be solids such as dusts, granules, or wettable powders, or they can be liquids such as solutions, aerosols, or emulsifiable concentrates.

For example, dusts can be prepared by grinding and blending the active compound with a solid inert carrier such as the talcs, clays, silicas, prophyllite, and the like. Granular formulations can be prepared by impregnating the compound, usually dissolved in a suitable solvent, onto and into granulated carriers such as the attapulgites or the vermiculites, usually of a particle size range of from about 0.3 to 1.5 millimeters. Wettable powders, which can be dispersed in water or oil to any desired concentration of the active compound, can be prepared by incorporating wetting agents into concentrated dust compositions.

In some cases the active compounds are sufficiently soluble in common organic solvents such as kerosene or xylene so that they can be used directly as solutions in these solvents. Frequently, solutions of herbicides can be dispersed under superatmospheric pressure as aerosols. However, preferred liquid herbicidal formulations are emulsifiable concentrates, which comprise an active compound according to this invention and as the inert carrier, a solvent and an emulsifier. Such emulsifiable concentrates can be extended with water and/or oil to any desired concentration of active compound for application as sprays to the site of the weed infestation. The emulsifiers most commonly used in these concentrates are nonionic or mixtures of nonionic with anionic surface-active agents. With the use of some emulsifier systems, an inverted emulsion (water in oil) can be prepared for direct application to weed infestations.

A typical herbicidal formulation according to this invention is illustrated by the following example, in which the quantities are in parts by weight.

EXAMPLE II

PREPARATION OF A DUST

Product of Example I: 10
Powdered Talc: 90

The above ingredients are mixed in a mechanical grinder-blender and are ground until a homogeneous, freeflowing dust of the desired particle size is obtained. This dust is suitable for direct application to the site of the weed infestation.

d. Use of Compounds Alone or in Mixtures

Although all of the compounds described herein and represented by the general formula described herein are useful as herbicides, some of these are preferred such as methyl N-[5-(2-chloro-4-trifluoromethylphenoxy)-2-nitrobenzoyl]carbamate, and are better for applications against weeds. In general, all of the compounds described herein may be used either alone or together in mixtures. When used in mixtures, the amount or ratio of one compound to another may vary from 0.01 to 100.

e. Manner of Application of the Compounds of This Invention

The compounds of this invention can be applied as herbicides in any manner recognized by the art. One method for the control of weeds comprises contacting the locus of said weeds with a herbicidal formulation comprised of an inert carrier and one or more of the compounds of this invention as an essential active ingredient, in a quantity which is herbicidally toxic to said weeds. The concentration of the new compounds of this invention in the herbicidal formulations will vary greatly with the type of formulation and the purpose for which it is designed; but generally the herbicidal formulations will comprise from about 0.05 to about 95 percent by weight of the active compounds of this invention. In a preferred embodiment of this invention, the herbicidal formulations will comprise from about 5 to 75 percent by weight of the active compound. The formulations can also comprise other pesticides, such as insecticides, nematocides, fungicides, and the like; stabilizers, spreaders, deactivators, adhesives, stickers, fertilizers, activators, synergists, and the like.

The compounds of the present invention are also useful when combined with other herbicides and/or defoliants, desiccants, growth inhibitors, and the like in the herbicidal formulations heretofore described. These other materials can comprise from about 5 percent to about 95 percent of the active ingredients in the herbicidal compositions. Use of combinations of the present invention provide herbicidal formulations which are more effective in controlling weeds and often provide results unattainable with separate formulations of the individual herbicides.

f. Examples of Other Pesticides and Herbicides for Combinations

The other herbicides, defoliants, desiccants, and plant growth inhibitors, with which the compounds of this invention can be used in the herbicidal formulations to control weeds, can include: chlorophenoxy herbicides such as 2,4-D, 2,4,5-T, MCPA, MCPB, 4-(2,4-DB), 2,4-DEB, 4-CPB, 4-CPA, 4-CPP, 2,4,6-TB, 2,4,5-TES, 3,4-DA, silvex and the like; carbamate herbicides such as IPC, CIPC, swep, barban, BCPC, CEPC, CPPC, and the like; thiocarbamate and dithiocarbamate herbicides such as CDEC, metam sodium, EPTC, diallate, PEBC, pebulate, vernolate and the like; substituted urea herbicides such as norea, siduron, dichloroal urea, chloroxuron, cycluron, fenuron, monuron TCA, diuron, linuron, monolinuron, neburon, buturon, trimeturon, and the like; symmetrical triazine herbicides such as simazine, chlorazine, desmetryne, norazine, ipazine, prometryn, atrazine, trietazine, simetone, prometone, propazine, ametryne, and the like; chloroacetamide herbicides such as alpha-chloro-N,N-dimethylacetamide, CDEA, CDAA, alpha-chloro-N-isopropylacetamide, 2-chloro-N-isopropylacetanilide, 4-(chloroacetyl)morpholine, 1-(chloroacetyl)piperidine, and the like; chlorinated aliphatic acid herbicides such as TCA, dalapon, 2,3-dichloro propionic acid, 2,2,3-TPA, and the like; chlorinated benzoic acid and phenylacetic acid herbicides such as 2,3,6-TBA, 2,3,5,6-TBA, dicamba, tricamba, amiben, fenac, PBA, 2-methoxy-3,5-dichlorophenylacetic acid, methoxy-2,6-dichlorophenylacetic acid, 2-methoxy-3,5,6-trichlorophenylacetic acid, 2,5-dichloro-3-nitrobenzoic acid, dual, metribuzin and the like; and such compounds as aminotriazole, maleic hydrazide, phenyl mercuric acetate, endothall, biuret, technical chlordane, dimethyl 2,3,5,6-tetrachlorotere phthalate, diquat, erbon, DNC, CNBP, dichlobenil, DPB, diphenamid, dipropalin, trifluralin, solan, dicryl, merphos, DMPA, DSMA, MSMA, potassium azide, acrolein, benefin, bensulfide, AMS, bromacil, 2-(3,4-dichlorophenyl)-4-methyl-1,2,4-oxadiazolidine-3,5-dione, bromoxynil, cacodylic acid, CMA, CPMF, cypromid, DCB, DCPA, dichlone, diphenatril, DMTT, DNAP, EXD, ioxynil, isocil, potassium cyanate, MAA, MAMA, MCPES, MCPP, MH, molinate, NPA, paraquat, PCP, picloram, DPA, PCA, pyrichlor, sesone, terbacil, terbutol, TCBA, LASSO, planavin, sodium tetraborate, calcium cyanamide, DEF, ethyl xanthogen disulfide, sindone, sindone B, propanil and the like. Such herbicides can also be used with the compositions of this invention in the form of their salts, esters, amides, and other derivatives whenever applicable to the particular parent compounds.

g. Examples of Herbicidal Control

The following examples illustrate the utility of the compounds described herein, for the control of weeds. These tests were conducted in a laboratory under standardized laboratory conditions and methods.

EXAMPLE III

When the compound of Example I, methyl N-[5-(2-chloro-4-trifluoromethylphenoxy)-2-nitrobenzoyl]carbamate, was applied preemergence at two pounds per acre against the weeds: *Sida spinosa* (L) (teaweed), *Setaria glauca* (L) (yellow foxtail), *Digitaria sanguinalis* (L) (large crabgrass), *Sorghum halepense* (L) (johnsongrass), *Sesbania spp.* (coffeeweed), *Abutilon theophrasti* (L) (velvetleaf), and *Echinochloa crusgalli* (L) (barnyardgrass), all of the weeds were severely injured or killed at the end of twenty-one (21) days.

It was discovered that the compounds, particularly the preferred compound methyl N-[5-(2-chloro-4-trifluoromethylphenoxy)-2-nitrobenzoyl]carbamate, were safe to apply preemergence at rates of five pounds per acre or lower to control weeds in crops such as cotton, soybeans, and tomatoes.

While the invention has been described with reference to specific details of certain illustrative embodiments, it is not intended that it shall be limited thereby except insofar as such details appear in the accompanying claims.

I claim:

1. A compound represented by Formula I:

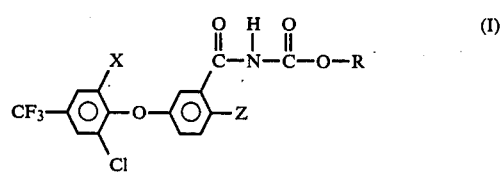

wherein:

X is hydrogen (H), chloro (Cl), or bromo (Br);
Z is nitro (NO₂), halogen, or cyano (CN); and
R is an alkyl of up to four carbon atoms or

where A is halogen, an alkyl of up to three carbon atoms, an alkoxy of up to three carbon atoms, an alkylthio of up to three carbon atoms, cyano (CN), trifluoromethyl (CF₃), nitro (NO₂), or CO₂R², where R² is an alkyl of up to four carbon atoms, and n is an integer of 0, 1, 2, or 3.

2. The compound as recited in claim 1 wherein R is

3. The compound as recited in claim 1 wherein R is an alkyl of up to four carbon atoms.

4. The compound as recited in any of claims 1, 2, or 3 wherein Z is nitro (NO₂).

5. The compound as recited in claim 4 wherein X is hydrogen.

6. The compound as recited in claim 1, which is Methyl N-[5-(2-chloro-4-trifluoromethylphenoxy)-2-nitrobenzoyl]carbamate.

7. A method of controlling weeds which comprises: contacting the weeds with a herbicidally effective amount of a compound represented by Formula I:

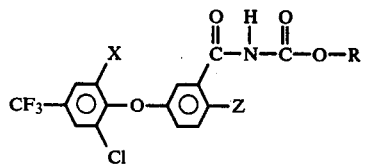

wherein:

X is hydrogen (H), chloro (Cl), or bromo (Br);
Z is nitro (NO₂), halogen, or cyano (CN); and
R is an alkyl of up to four carbon atoms or

wherein A is halogen, an alkyl of up to three carbon atoms, an alkoxy of up to three carbon atoms, an alkylthio of up to three carbon atoms, cyano (CN), trifluoromethyl (CF₃), nitro (NO₂), or CO₂R², where R² is an alkyl of up to four carbon atoms, and n is an integer of 0, 1, 2, or 3.

8. The method as recited in claim 7 wherein R is

9. The method as recited in claim 7 wherein R is an alkyl of up to four carbon atoms.

10. The method as recited in claims 7, 8, or 9 wherein Z is nitro (NO₂).

11. The method as recited in claim 10 wherein X is hydrogen (H).

12. The method as recited in claim 7 wherein the compound is Methyl N-[5-(2-chloro-trifluoromethylphenoxy)-2-nitrobenzoyl]carbamate.

13. The method as recited in claim 10 wherein the herbicidally effective amount is an amount which is also safe to crops.

14. The method as recited in claim 11 wherein the herbicidally effective amount is an amount which is also safe to crops.

15. The method as recited in claim 12 wherein the herbicidally effective amount is an amount which is also safe to crops.

* * * * *